(12) United States Patent
Foucault et al.

(10) Patent No.: US 7,553,421 B2
(45) Date of Patent: Jun. 30, 2009

(54) METHOD FOR OPTIMALLY SIZING CELLS OF A CENTRIFUGAL PARTITION CHROMATOGRAPHY DEVICE

(75) Inventors: Alain Foucault, Saint-Nazaire (FR); Jack Legrand, Saint-Nazaire (FR); Luc Marchal, Gournay-sur-Aronde (FR); Daniel Durand, Rueil-Malmaison (FR)

(73) Assignees: Institut Francais du Petrole, Rueil Malmaison Cedex (FR); Universite de Nantes, Nantes Cedex (FR)

( * ) Notice: Subject to any disclaimer, the term of this patent is extended or adjusted under 35 U.S.C. 154(b) by 0 days.

(21) Appl. No.: 10/593,774

(22) PCT Filed: Mar. 17, 2005

(86) PCT No.: PCT/FR2005/000652

§ 371 (c)(1),
(2), (4) Date: May 2, 2007

(87) PCT Pub. No.: WO2005/093406

PCT Pub. Date: Oct. 6, 2005

(65) Prior Publication Data

US 2008/0035546 A1   Feb. 14, 2008

(30) Foreign Application Priority Data

Mar. 23, 2004   (FR) .................................. 04 02978

(51) Int. Cl.
*B01D 15/08* (2006.01)
(52) U.S. Cl. ...................... 210/657; 210/635; 210/198.2
(58) Field of Classification Search ................ 210/635, 210/657, 198.2, 198.3; 422/70
See application file for complete search history.

(56) References Cited

U.S. PATENT DOCUMENTS 4,877,523 A   10/1989   Nunogaki (Continued)

OTHER PUBLICATIONS

Google Translation of Apr. 11, 2008 of the first three full paragraphs of p. 5 of GEPEA Resultants 2001 Internet Article, Online Mar. 2, 2003, pp. 1-7.*

(Continued)

*Primary Examiner*—Ernest G Therkorn
(74) *Attorney, Agent, or Firm*—Antonelli, Terry, Stout & Kraus, LLP.

(57) ABSTRACT

Method for sizing the cells of a centrifugal liquid-liquid chromatography "column" (CPC column) consisting of stacked discs on which the cells connected in cascade (in series) by small channels are engraved. Rotation of the stack creates a high centrifugal acceleration field which makes it possible to keep a liquid phase referred to as stationary phase motionless, whereas a mobile phase circulates along the CPC column. The cells are three-dimensional, with two dimensions (L, l) of the cells oriented in a plane substantially normal to the axis of rotation ($\Omega$) of the disc and a third dimension (e) oriented in a direction substantially parallel to the axis of rotation, and selected so as to be at least equal to one of the other two dimensions (L, l), thus providing higher efficiency. When the scale of the devices has to be changed, the size of the cells is modified ensuring that, in any case, this third dimension (e) is favored so as to be as great as possible.

Applications: design of analytic or preparative chromatography devices.

2 Claims, 2 Drawing Sheets

U.S. PATENT DOCUMENTS 6,537,452 B1  3/2003  de La Poype et al.
2004/0173534 A1* 9/2004  Margraff et al. ............ 210/656

OTHER PUBLICATIONS

Muratama et al.: A new centrifugal counter-current chromatograph and its application Journal of Chromatography, vol.: 239, Apr. 30, 1982 pp. 643-649.

Marchal et al.: "Influence of flow patterns on chromatographic efficiency in centrifugal partition chromatography" Journal or Chromatography A, vol. 869, Feb. 11, 2000, pp. 339-352.

Anonymous: GEPEA Resultats 2001 Internet Article, Online! Mar. 2, 2003, pp. 1-7.

* cited by examiner

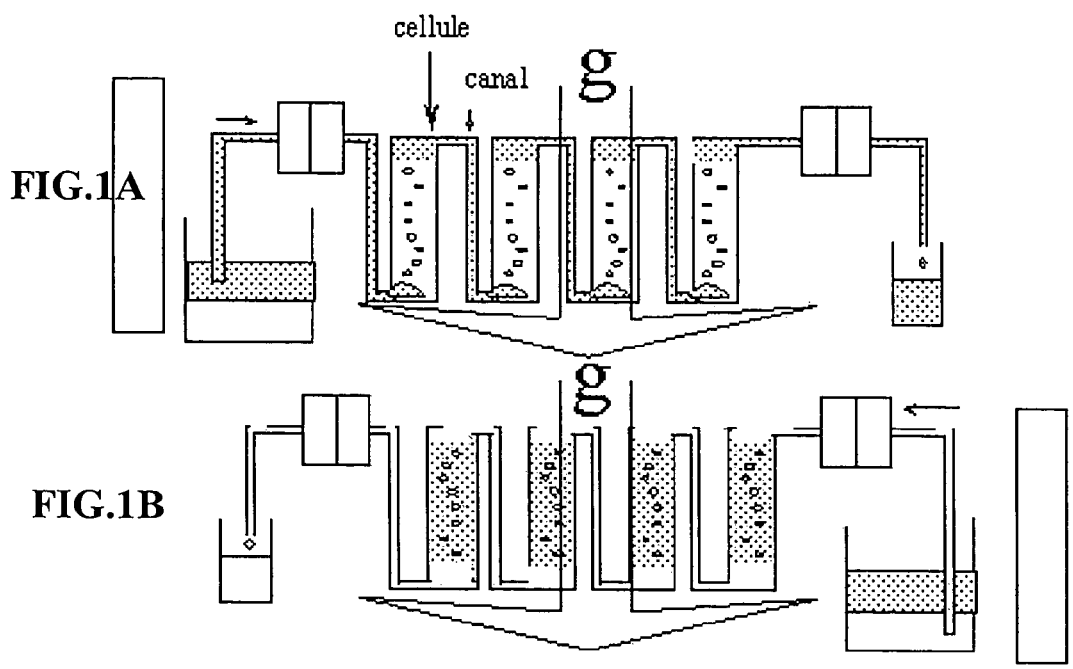
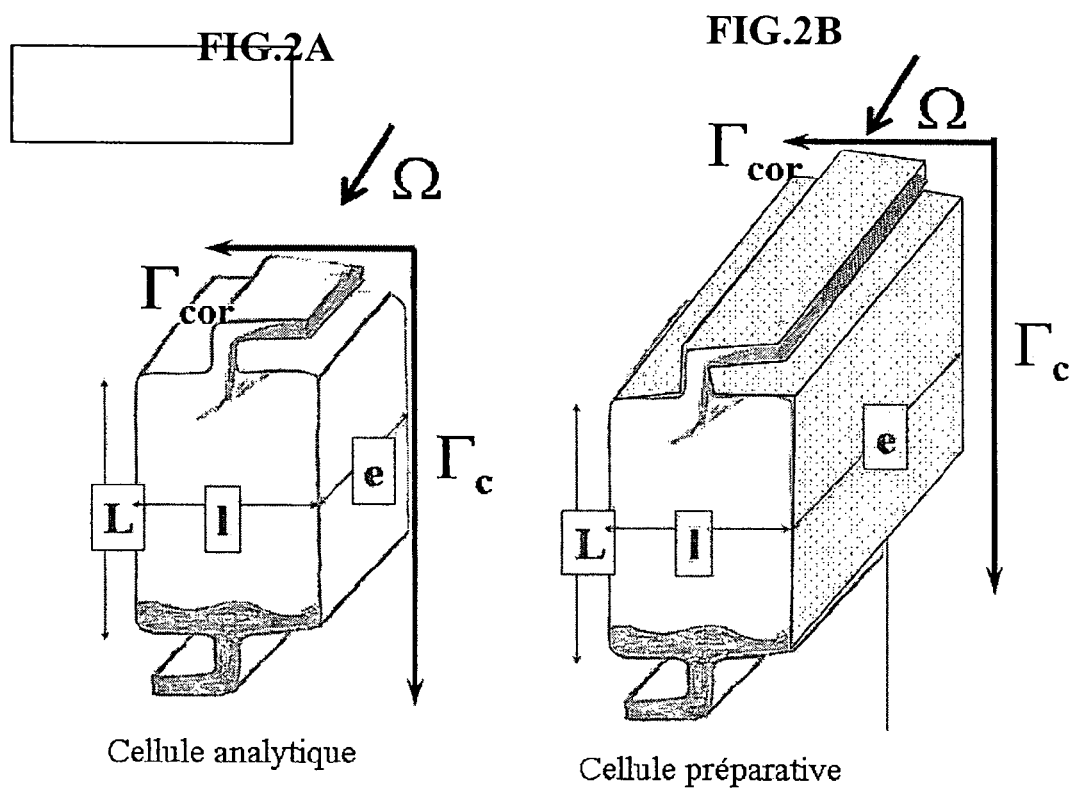
Cellule analytique | Cellule préparative

METHOD FOR OPTIMALLY SIZING CELLS OF A CENTRIFUGAL PARTITION CHROMATOGRAPHY DEVICE

REFERENCE TO RELATED APPLICATIONS

This application is a 371 of PCT/FR05/00652 filed Mar. 17, 2005.

FIELD OF THE INVENTION

The present invention relates to a method of sizing cells of a centrifugal liquid-liquid chromatography device.

This type of device, consisting of the interconnection in series of one or more chain(s) of cells, is used to carry out separation of the constituents of a feedstock in liquid solution made up of at least two constituents having different partition coefficients so that they are carried along at unequal velocities by the mobile phase which can be one or the other of the liquid phases.

BACKGROUND OF THE INVENTION

A known technique for separating constituents A and B in solution in a liquid mixture consists in injecting it into a "chromatographic column" subjected to a centrifugal force, so designed that one of the liquid phases can be percolated into the other liquid phase and vice versa (chromatography referred to as CCC or CPC).

In practice, as shown notably in patents FR-2,791,578, U.S. Pat. No. 4,551,251, U.S. Pat. No. 4,877,523 or U.S. Pat. No. 4,857,187, this type of system comprises one or more stacks of discs driven in rotation. Each one comprises (FIG. 4), in the thickness and over the entire periphery thereof, a succession of cells CE arranged in a radial or oblique direction and connected in series by a set of circuits of fine winding channels B at the ends of each cell. The circuits of all the discs communicate with one another. Cells CE and their communication circuits B are filled with a stationary liquid phase that is kept in place by the centrifugal force and with another mobile liquid phase that percolates through the stationary phase.

Rotation of the stack creates a high centrifugal acceleration field that allows the stationary liquid phase to remain fixed whereas the mobile phase circulates in a mode referred to as ascending (FIG. 1A) if it is lighter than the stationary phase, and in descending mode (FIG. 1B) if it is heavier.

The chromatographic process, i.e. partition of the molecules to be purified between the two liquid phases, takes place in each cell, and mass transfer is favoured by a good dispersion of the mobile phase flowing from the channel into each cell.

To obtain better separation, it is possible for example, as described in patent application FR-03/08,076, to inject the feedstock at an intermediate point of the chain of cells making up the column, and to carry out alternate cycles of two stages, with a first stage during a first time interval where a lighter solvent is injected through a first end of the device and a first component is collected at a second end of the device, and a second stage during a second time interval where a heavier solvent is injected through the second end of the device and a second constituent is collected at the first end. The respective lengths of the first and of the second stage and/or the rates of injection of the lighter solvent and of the heavier solvent are adjusted according to the constituents of the mixture so as to obtain optimum separation.

Whatever the shape thereof, each CPC cell can be characterized (FIG. 2A) by its length L, measured in a radial direction (or close to a radial direction), by its width l, measured in a direction normal (or close) to the radial direction, these first two quantities being measured in a plane normal to axis of rotation $\Omega$, and by its thickness e, measured along a direction parallel (or close) to the axis of rotation.

It can be easily checked that selection of these three dimensions for a given cell volume has a great impact on the separation efficiency obtained. The problem of selecting the right dimensions for the cells arises when an efficient separation system is to be designed, and also when the size thereof is to be changed to switch from an analytic type installation to an industrial type installation, or vice versa, while keeping the same efficiency.

SUMMARY OF THE INVENTION

The object of the method according to the invention is sizing of the cells of a centrifugal liquid-liquid chromatography column comprising a network of three-dimensional cells interconnected in series and communicating with liquid phase circulation means, the cells being distributed over the periphery of at least one disc driven in rotation, two dimensions of the cells being oriented in a plane substantially normal (or close) to the axis of rotation of the disc. For higher efficiency and yield purposes, the third dimension (e) arranged in a direction substantially parallel (or close) to the axis of rotation is selected so as to be at least equal to one of the other two dimensions (L, l) and preferably greater.

In order to increase the scale of chromatography devices (for example to change from an analytic chromatography device to an industrial device), the size of the cells is preferably increased by increasing essentially the third dimension (e) thereof and additionally, if necessary, the other two dimensions (L, l).

On the other hand, in order to reduce the scale of chromatography devices (to change from an industrial chromatography device to an analytic device), the size of the cells is preferably decreased by decreasing essentially the third dimension (e) thereof and additionally, if necessary, the first and the second dimension (L, l) so as to keep the third dimension (e) at least equal to one of the other two dimensions (L, l).

As shown in detail in the description hereafter, this sizing rule allows the efficiency and the productivity of chromatography devices to be increased.

BRIEF DESCRIPTION OF THE FIGURES

Other features and advantages of the method according to the invention will be clear from reading the description hereafter of an embodiment given by way of non limitative example, with reference to the accompanying figures wherein:

FIGS. 1A, 1B show a flowsheet of a CPC type separation device comprising several interconnected cells associated with fluid circulation means, that is subjected to an acceleration g, in cases where the mobile phase circulates in a mode referred to as ascending (FIG. 1A) and where the mobile phase flows in a mode referred to as descending (FIG. 1B), depending on whether it is lighter or heavier than the stationary phase, FIGS. 2A, 2B show two examples of cells of different sizes with non-homothetic dimensions.

DETAILED DESCRIPTION

Figure 3:
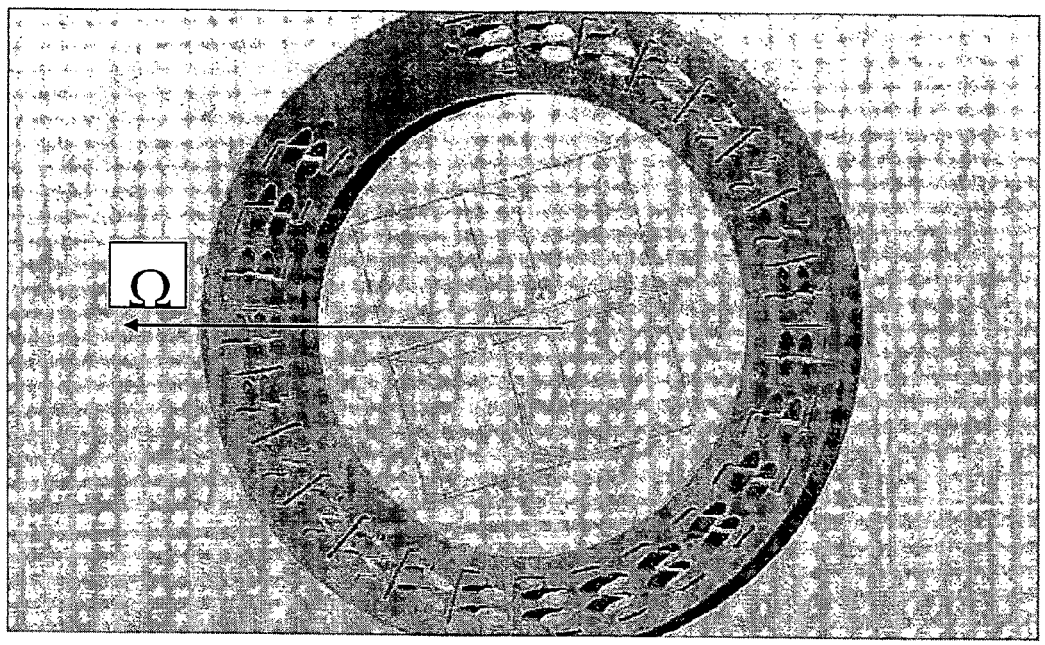
FIG. 3 shows an example of a disc with cells engraved in the thickness thereof, and FIG. 4 diagrammatically shows cells arranged all around a disc.
Figure 4:
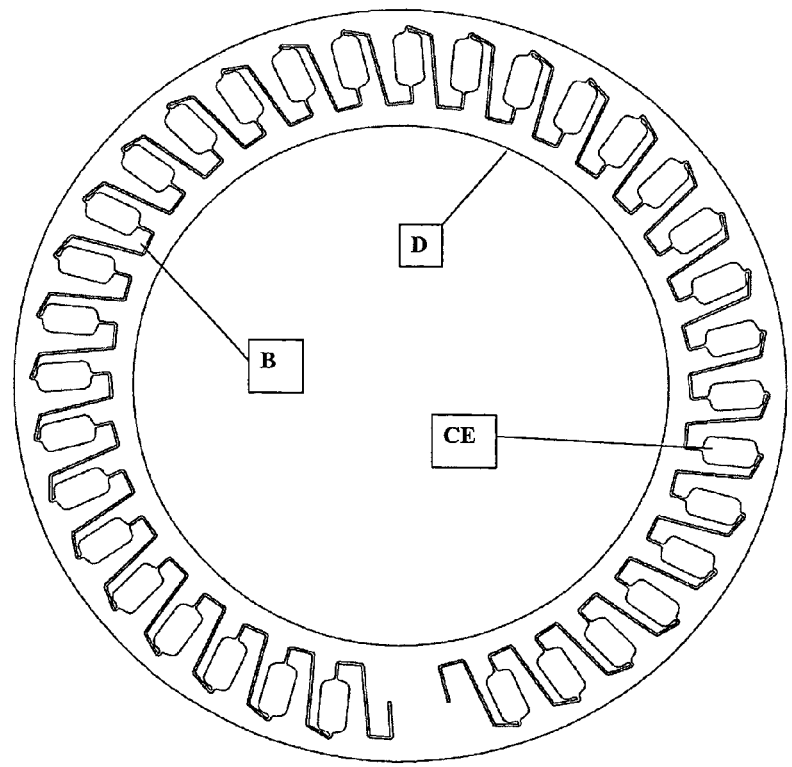

It has been confirmed that a mobile phase film fed into the top of a cell has a trajectory and a behaviour that are closely linked with the three dimensions L, l and e. The orientation (FIG. 2) of the Coriolis acceleration vector $\Gamma_{cor}$, which is of great significance for the evolution of the flow regimes in the cells, fundamentally differentiates dimensions l and e since it is oriented in the direction of l and not at all in the direction of e.

Study results show that, considering the locations of the inlets linking each cell to the channels that connect it to the next and following cells, a variation of the three quantities L, l and e has a very different repercussion on the hydrodynamic characteristics of the flow in the cell.

The nature of the flows (spray or oscillating film type) is very greatly correlated with the linear velocity of inflow, Ve, of the mobile phase in the cell, which is proportional to the cube root of the volume flow rate/thickness e ratio; this parameter (Ve) is independent of L and l, and it assigns to e a fundamental role that has never been described so far. Cell profiles allowing to work with high flow rates by causing disperse flows while increasing the efficiency and the productivity of a CPC device (shorter analysis time and/or higher hourly yield) therefore have to be preferred.

Detailed studies have allowed to show:

a) that a great increase in thickness e in relation to the possible variations of L and l will have favourable consequences on the flows while allowing the cell to be given a size in accordance with common practice on the preparative or industrial scale, and b) that thickness e preferably has to be greater than or at least equal to all the other dimensions of the cell.

It has been checked that a separation system with such cells favouring thickness e is much more efficient (in the chromatographic sense) than cells where the two dimensions L and l are greater, which is the case in the systems currently available on the market.

The hydrodynamic behaviour of the fluids present in a centrifugal partition chromatography (CPC) column is closely linked, as shown above, with the conformation of the cells. Thus, the change in size of the cells (larger size for use on the industrial scale or smaller size for an analytic use) by simple homothety does not have good results.

Therefore, if the size of CPC cells (cell referred to as analytic, FIG. 2A for example) has to be increased for industrial applications, whatever the shape thereof, thickness e essentially has to be increased, and length L and/or width l (cell referred to as preparative, FIG. 2B) can be increased secondarily.

By way of non limitative example, thicknesses e at least twice as great as the other two dimensions can be selected.

The invention claimed is:

1. A method for sizing the cells of centrifugal liquid-liquid chromatography devices comprising a network of three-dimensional cells interconnected in series and communicating with liquid circulation means, the cells being distributed over the periphery of at least one disc driven in rotation, a first and a second dimension (L, l) of the cells being oriented in a plane substantially normal to the axis of rotation ($\Omega$) of the disc, characterized in that, in order to increase the scale of chromatography devices, the size of the cells is changed by increasing essentially a third dimension (e) of the cells arranged in a direction substantially parallel to the axis of rotation and additionally, if necessary, the other two dimensions (L, l) so that the third dimension (e) is at least equal to one of the other two dimensions (L, l).

2. A method for sizing the cells of centrifugal liquid-liquid chromatography devices comprising a network of three-dimensional cells interconnected in series and communicating with liquid circulation means, the cells being distributed over the periphery of at least one disc driven in rotation, a first and a second dimension (L, l) of the cells being oriented in a plane substantially normal to the axis of rotation ($\Omega$) of the disc, characterized in that, in order to reduce the scale of chromatography devices, the size of the cells is changed by decreasing essentially a third dimension (e) of the cells arranged in a direction substantially parallel to the axis of rotation and additionally, if necessary, the first and the second dimension (L, l) so as to keep the third dimension (e) at least equal to one of the other two dimensions (L, l).

* * * * *